(12) United States Patent
Tanaka et al.

(10) Patent No.: US 9,658,128 B2
(45) Date of Patent: May 23, 2017

(54) DEFECT INSPECTION METHOD

(71) Applicant: KABUSHIKI KAISHA TOSHIBA, Minato-ku, Tokyo (JP)

(72) Inventors: Akira Tanaka, Tokyo (JP); Masaya Hirashima, Tokyo (JP); Satoru Yasui, Tokyo (JP); Mayumi Naito, Kawasaki Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 15/010,536

(22) Filed: Jan. 29, 2016

(65) Prior Publication Data
US 2017/0102285 A1    Apr. 13, 2017

(30) Foreign Application Priority Data
Oct. 8, 2015  (JP) .................. 2015-200437

(51) Int. Cl.
G01N 23/05   (2006.01)
G01M 3/20    (2006.01)

(52) U.S. Cl.
CPC .............. *G01M 3/20* (2013.01); *G01N 23/05* (2013.01)

(58) Field of Classification Search
USPC ............. 250/251, 302, 303, 492.1, 493.1
See application file for complete search history.

(56) References Cited

U.S. PATENT DOCUMENTS

| | | | |
|---|---|---|---|
| 7,796,720 B1 * | 9/2010 | Rubbia ................. | G21G 1/06 376/156 |
| 8,735,844 B1 * | 5/2014 | Khaykovich ........... | G21K 1/06 250/390.1 |
| 2003/0152186 A1 * | 8/2003 | Jurczyk ................. | G21B 1/19 376/109 |

FOREIGN PATENT DOCUMENTS

| | | |
|---|---|---|
| JP | 2005-098875 | 4/2005 |
| JP | 2007-178370 | 7/2007 |
| JP | 2008-202989 | 9/2008 |
| JP | 2011-169791 | 9/2011 |

* cited by examiner

*Primary Examiner* — Nicole Ippolito
(74) *Attorney, Agent, or Firm* — Knobbe, Martens, Olson & Bear, LLP

(57) ABSTRACT

A defect inspection method according to an embodiment has: exposing a target object to a tracer having higher absorptance for a neutron ray than the target object; radiating the neutron ray to the target object exposed to the tracer; generating at least one neutron image based on the neutron ray having penetrated the target object exposed to the tracer; and detecting a defect of the target object based on the generated at least one neutron image.

7 Claims, 6 Drawing Sheets

DEFECT INSPECTION METHOD

CROSS-REFERENCE TO RELATED APPLICATION

This application is based upon and claims the benefit of priority from Japanese Patent Application No. 2015-200437, filed on Oct. 8, 2015; the entire contents of which are incorporated herein by reference.

FIELD

An embodiment described herein relate generally to a defect inspection method.

BACKGROUND

In general, many components mounted on an electronic device are joined by soldering such as surface mounting. However, a soldered portion such as a solder bump applied to surface mounting is gradually deteriorated by thermal fatigue arising from operation of the electronic device, and a crack or the like extends and a fracture occurs depending on the circumstances, to sometimes cause continuity failure.

So, in order for prior evaluation of a deterioration condition (extension of a crack or the like) of a soldered portion or in order to analyze a mechanism of defect occurrence in the soldered portion, a defect inspection method enabling a nondestructive inspection is utilized. In the inspection method of such a kind, inspection is carried out by visualizing a defect such as a crack occurring in a soldered portion by means of a see-through image generated by an X-ray observation apparatus or an X-ray CT (Computed Tomography) apparatus.

However, in the aforementioned defect inspection method, since an X-ray absorptance (X-ray attenuation factor) of solder is high, the soldered portion comes out dark overall on the see-through image by the X-ray. Thus, it is difficult to detect a comparatively small crack or the like occurring in the soldered portion. Note that, other than the above, there is a request for enabling accurate detection of a defect occurring in a resin molded article or a metal component other than solder.

DETAILED DESCRIPTION

A problem to be solved by the present invention is to provide a defect inspection method capable of heightening a detection accuracy of a defect which may occur in an inspection object.

A defect inspection method according to an embodiment has: exposing a target object to a tracer having higher absorptance for a neutron ray than the target object; radiating the neutron ray to the target object exposed to the tracer; generating at least one neutron image based on the neutron ray having penetrated the target object exposed to the tracer; and detecting a defect of the target object based on the generated at least one neutron image.

Figure 1:
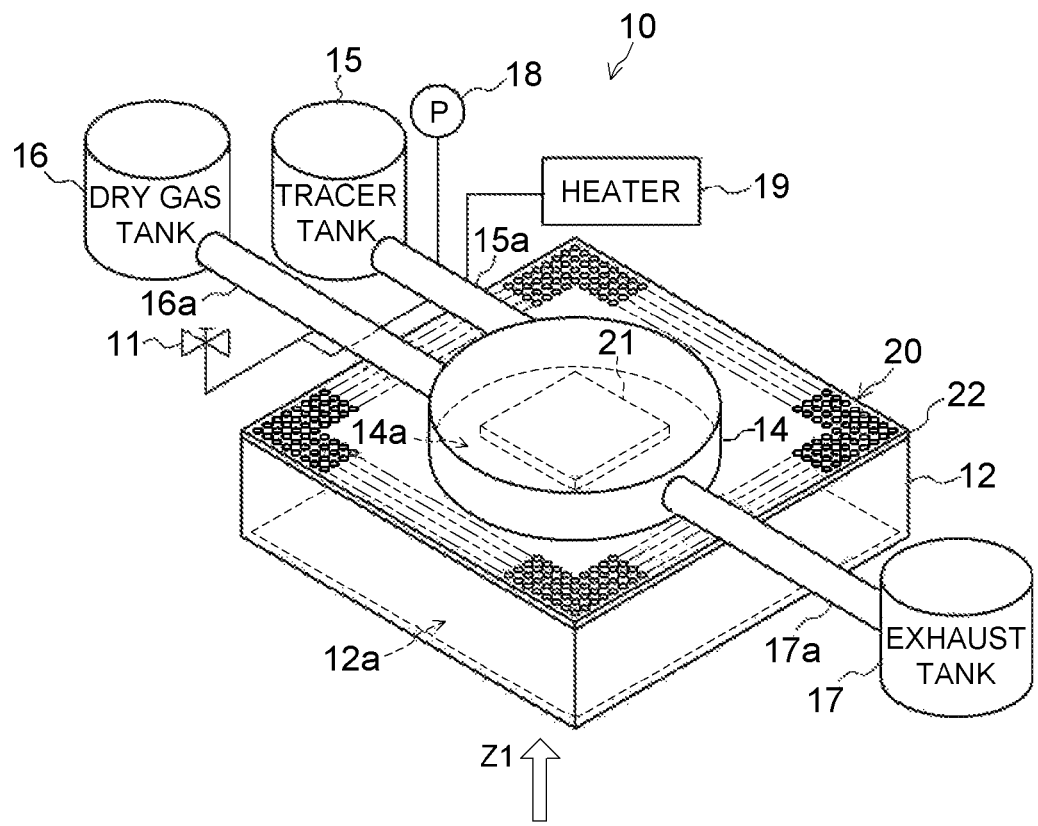
FIG. 1 is a diagram schematically showing a configuration of a defect inspection device according to an embodiment.
Figure 2:
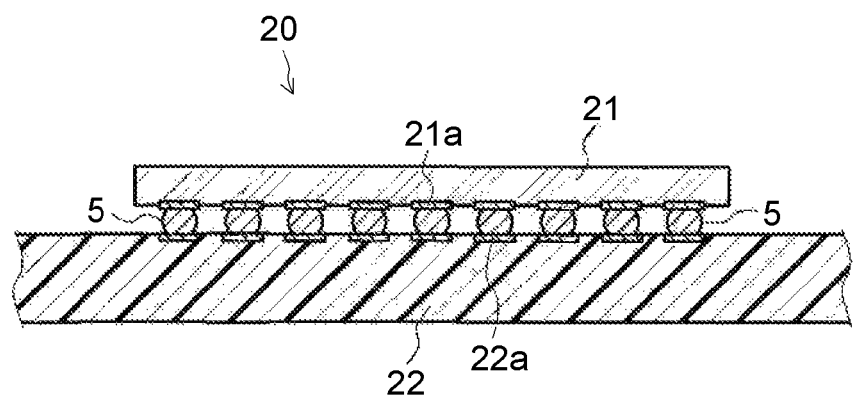
FIG. 2 is a cross-sectional view showing a configuration of an inspection object to be inspected by the defect inspection device of FIG. 1.
Figure 3:
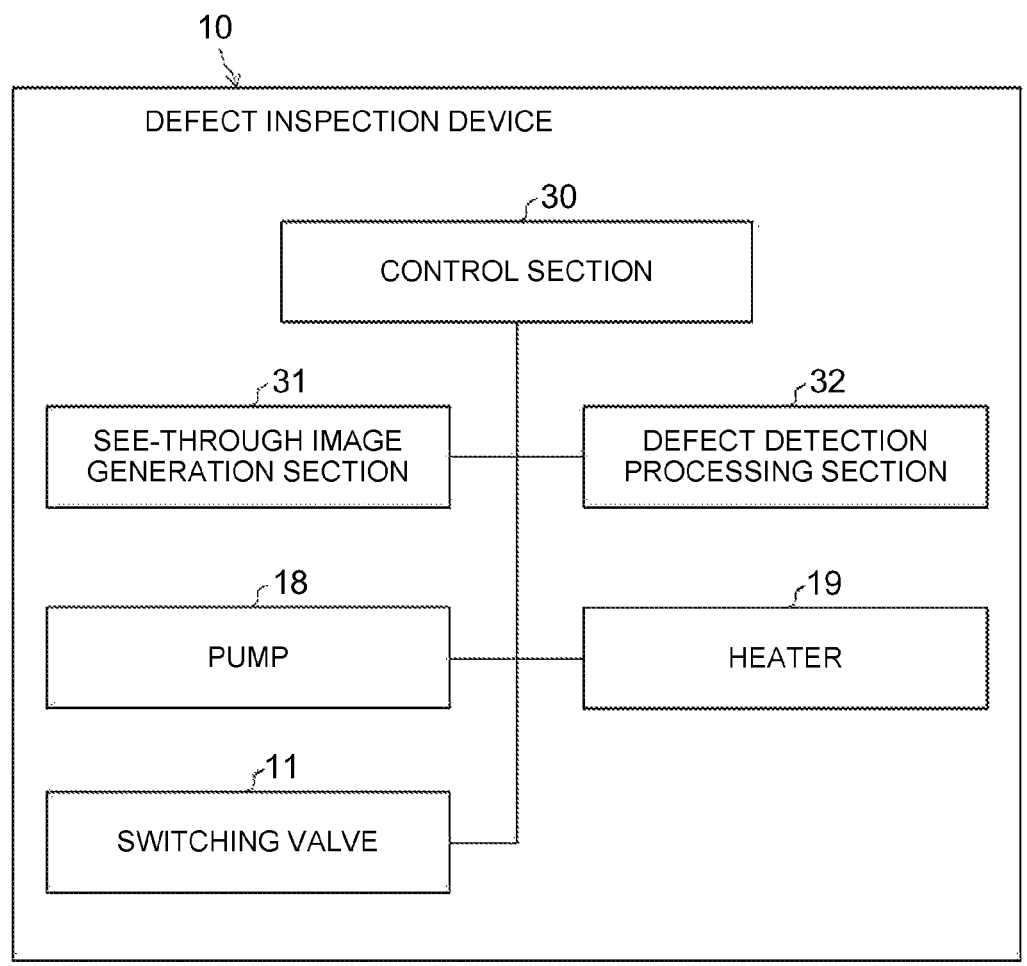
FIG. 3 is a block diagram functionally showing a major configuration of the defect inspection device of FIG. 1.

Hereinafter, the embodiment will be described based on drawings. As shown in FIG. 1 to FIG. 3, a defect inspection device 10 of the present embodiment is a device for accurately visualizing and detecting a defect such as a crack which may exist in an electronic component 20 (solder bump 5 as an inspection object which constitutes a part of the electronic component 20) by using a neutron ray which can be taken out in a large-scale synchrotron radiation facility such as Spring-8 (Super Photon ring-8 GeV), for example.

The defect inspection device 10 has, as shown in FIG. 1 and FIG. 3, a fixing holder 12, a chamber 14, a tracer tank 15, a dry gas tank 16, an exhaust tank 17, pipes 15a, 16a, 17a, a pump 18, a heater 19, a switching valve 11, a control section 30, a see-through image generation section (a neutron image generation section) 31, and a defect detection processing section 32.

As shown in FIG. 1 and FIG. 2, the electronic component 20 is a CPU (Central Processing Unit) for a PC (Personal Computer), for example, which has a configuration where a die (bare chip) 21 is mounted on an interposer (substrate) 22. The interposer (substrate) 22 and the die (bare chip) 21 are flip-chip connected to each other via a plurality of bumps (inspection objects/target objects) 5 and electrode pads 21a, 22a.

Further, thermal fatigue is given to this electronic component 20 in advance. The thermal fatigue is given as a result that thermal change of −20° C. to +80° C. is given to the electronic component for 30 minutes, for example, by using a thermal cycle test (TCT) device, and further that the thermal change is repeated 1000 cycles. The defect inspection device 10 of the present embodiment inspects existence/absence or the like of a crack which may occur in the above-described bump (inspection object) 5 in a non-destructive manner.

The fixing holder 12 is a support table for fixing the electronic component 20, as shown in FIG. 1, and is formed of stainless steel, for example, which does not have a hydrophilic property. Further, the fixing holder 12 has a clamping mechanism for clamping a peripheral portion of the rectangular electronic component 20 at 10 places, for example. The fixing holder 12 is able to fix the electronic component 20 with a high positioning accuracy of 100 nm order, for example.

Further, as shown in FIG. 1, the fixing holder 12 is constituted to have a rectangular rim shape of 300 mm in length width, 300 mm in breadth width, and 1 mm in thickness, for example. The fixing holder 12 has a rectangular through hole 12a running through in an arrow Z1 direction (vertically upward). A neutron ray taken out via a large-scale synchrotron radiation facility is radiated to the electronic component 20 including the solder bump (inspection object) 5 through the inside of the through hole 12a from the arrow Z1 direction (bottom portion side of the electronic component 20). Further, the fixing holder 12 has a temperature adjusting mechanism which materializes a heating function or a cooling function by having a heater, a controller, a thermocouple, or the like.

As shown in FIG. 1, the chamber 14 constitutes a hermetic space 14a between the chamber 14 and the interposer 22, and houses the die 21 including the plurality of solder bumps 5 in the hermetic space 14a. The chamber 14 is configured by carrying out silicone resin water repellent coating to a bottomed cylindrical (a petri dish-shaped) quartz container (or transparent resin container) of 70 mm in diameter and 10 mm in thickness, for example. Further, the chamber 14 is attached onto the interposer 22 via a double-sided adhesive tape or the like in a state where the die 21 including the solder bumps 5 is encircled while a peripheral portion in an opening part of the chamber 14 is adhered to the interposer 22.

The tracer tank 15 stores water such as heavy water ($D_2O$) and light water as a tracer. The tracer functions as a contrast medium of the see-through image by the neutron ray. The tracer tank 15 has a capacity of 500 ml or more, for example, and at least an inner surface thereof is coated with a fluorine resin (fluorocarbon resin) such as Teflon (registered trademark). Further, as shown in FIG. 1, the tracer tank 15, the dry gas tank 16, and the exhaust tank 17 are each connected to the chamber 14 via the pipes 15a, 16a, 17a of 3 mm in diameter, for example, at least inner surfaces of which are coated with fluorine resins.

As shown in FIG. 1, the pump 18 and the heater 19 are connected to the pipe 15a. The pump 18 supplies the tracer (water) in the tracer tank 15 into the chamber 14 (hermetic space 14a) via the pipe 15a. The heater 19 heats and vaporizes the tracer passing through the inside of the pipe 15a. In other words, the pump 18 and the heater 19 supply the tracer in a vaporized state into the hermetic space 14a in which the die 21 including the plurality of bumps 5 are housed.

The dry gas tank 16 houses dry nitrogen ($N_2$) gas. Further, as shown in FIG. 1, the switching valve 11 is connected to the pipe 15a and the pipe 16a, respectively. In other words, the switching valve 11 enables switching between a first state where a flow path inside the pipe 15a is opened and a flow path inside the pipe 16a is closed and a second state where the flow path inside the pipe 15a is closed and the flow path inside the pipe 16a is opened.

When the switching valve 11 has been switched to the first state, it is possible to supply the tracer in the tracer tank 15 into the chamber 14 via the pipe 15a. On the other hand, when the switching valve 11 has been switched to the second state, the dry nitrogen gas in the dry gas tank 16 is supplied into the chamber 14 (hermetic space 14a) via the pipe 16a. Further, in this case, the gas in the chamber 14 (hermetic space 14a) is discharged to the exhaust tank 17 via the pipe 17a. Thereby, it becomes possible to dry the inside of the chamber 14.

Further, as shown in FIG. 3, the control section 30 controls operation of the aforementioned switching valve 11, the pump 18, and the heater 19, and in addition, controls operation of the see-through image generation section 31 and the defect detection processing section 32.

Figure 4:
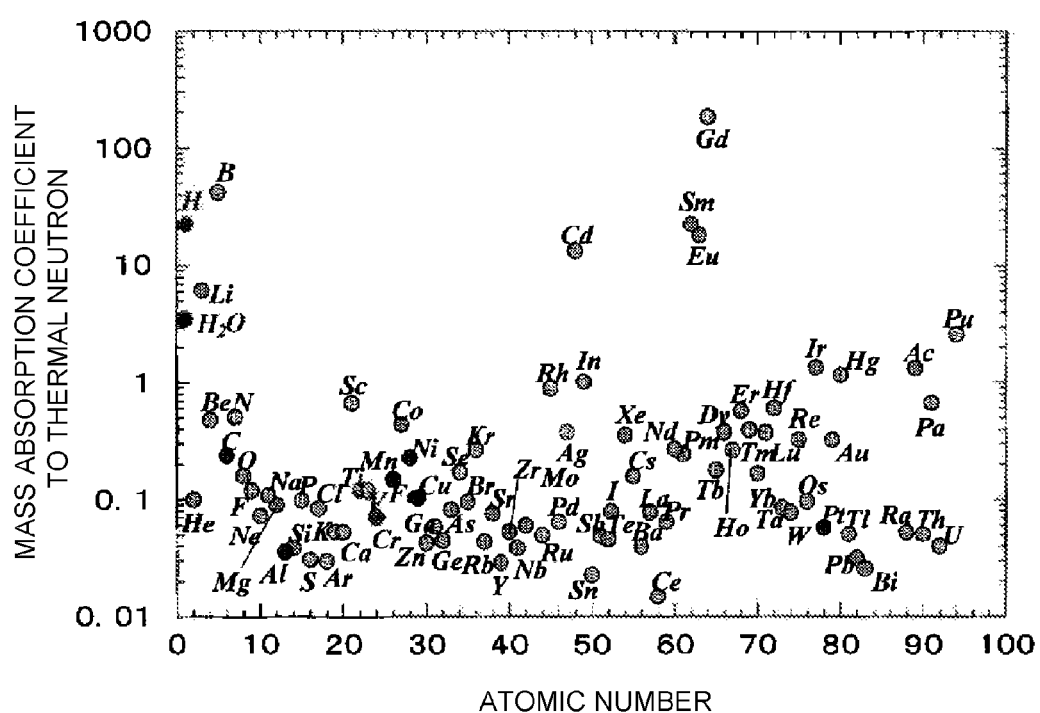
FIG. 4 is a chart showing a relation between a mass absorption coefficient to a thermal neutron and an atomic number of an element.

Here, FIG. 4 shows a relation between a mass absorption coefficient to a thermal neutron and an atomic number of an element. As shown in FIG. 4, water ($H_2O$) of light elements has a larger mass absorption coefficient (absorptance for a neutron ray) to a thermal neutron, compared with lead (Pb) and tin (Sn), which are heavy elements, being major constituents of the solder bump (inspection object) 5, and further, with a material (quartz: $SiO_2$) of the chamber 14 and a resin material, for example, to constitute the interposer 22.

In a case where a crack occurs in the solder bump 5 or the like, water as the tracer is made to permeate the crack, and a see-through image by a neutron ray is generated. In the generated see-through image, it is possible to obtain high contrast between the bump 5 main body which comes out light and the crack which the water (tracer) has permeated and comes out dark. Thereby, a defect such as a crack occurring in the solder bump 5 can be visualized (differentiated in relation to the solder bump 5 main body) accurately.

More specifically, the aforementioned see-through image generation section 31 has an image sensor (image pick up device) such as a FPD (flat panel detector), for example, on an upper side of the chamber 14. This image sensor receives the neutron ray having penetrated the electronic component 20 including the (tracer and) solder bump and the chamber 14 along the arrow Z1 direction, as shown in FIG. 1. The image sensor outputs a see-through image corresponding to the absorptance for the neutron ray in the penetrated material. In other words, in a state where the neutron ray is radiated to the electronic component 20 exposed to the tracer whose absorptance for the neutron ray is higher than that of the solder bump 5 (inspection object), the see-through image generation section 31 generates a see-through image (a neutron image) based on the neutron ray penetrating the electronic component 20 exposed to the tracer.

Figure 5:
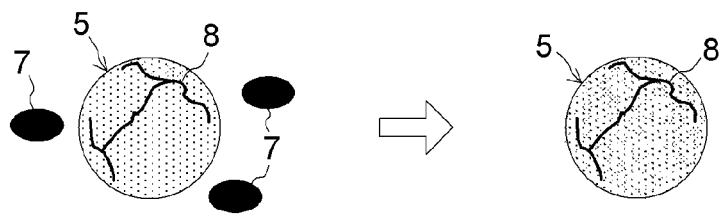
FIG. 5 is a diagram for explaining an example of a defect detection processing by the defect inspection device of FIG. 1.
Figure 6:
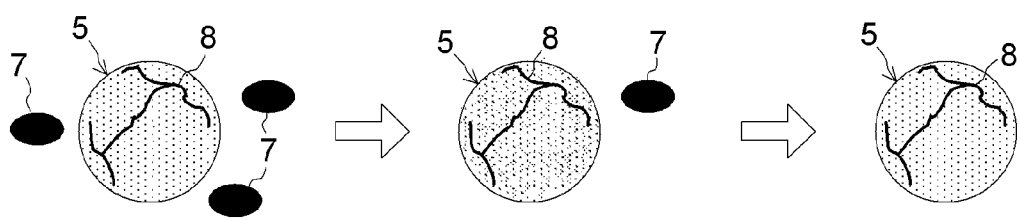
FIG. 6 is a diagram for explaining another defect detection processing different from the example of FIG. 5.
Figure 7:
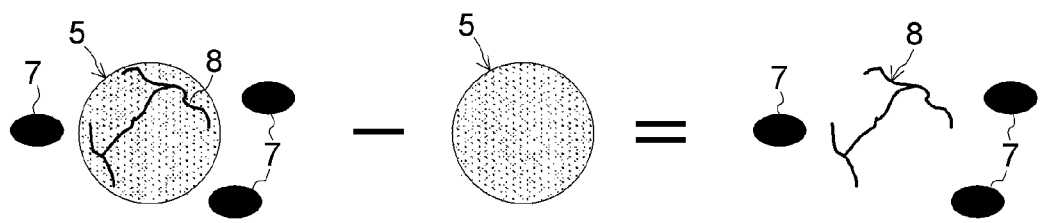
FIG. 7 is a diagram for explaining another defect detection processing different from the examples of FIG. 5 and FIG. 6.

On the other hand, the defect detection processing section 32 detects a defect such as a crack 8 which may exist in the solder bump (soldered portion) 5 by a defect detection processing selected from an integration observation processing, a time lapse processing, and a difference observation processing as shown in FIG. 5 to FIG. 7. Here, as shown in FIG. 1 and FIG. 3, the control section 30 controls the switching valve 11, the pump 18, and the heater 19 to expose the bump 5 to the vaporized tracer in the chamber 14, and next, controls the switching valve 11 to dry the vaporized tracer 7 in the chamber 14. Further, the control section 30 controls the see-through image generation section 31 to generate a plurality of see-through images by the neutron ray penetrating the inside of the chamber 14, in the course of the tracer 7 in the chamber 14 becoming dry. On the other hand, the defect detection processing section 32, based on the plurality of see-through images generated as above, detects the crack 8 which may exist in the solder bump 5. When the defect detection processing section 32 detects a place which the tracer (water) permeates in the solder bump 5 (detection object) based on the generated see-through image, the defect detection processing section 32 judges that the crack (defect) 8 has occurred in this place which the tracer permeates. Further, when the defect detection processing section 32 cannot detect a place which the tracer permeates, the defect detection processing section 32 judges that a crack has not occurred on the solder bump 5.

More specifically, as shown in FIG. 5, when the defect detection processing section 32 carries out the integration observation processing as the defect detection processing, in the course of the inside of the chamber 14 becoming dry, the defect detection processing section 32 acquires the plurality of see-through images sequentially generated by the see-though image generation section 31 in chronological order, for example, and, from the acquired plurality of see-through images, selects the plurality of see-through images, for example, from a time that the tracer 7 around the solder bump 5 becomes dry to a time that the tracer in the chamber 14 becomes completely dry. Further, with the selected plurality of see-through images being objects, the defect detection processing section 32 creates a histogram in which a color saturation indicating darkness of color (value of color saturation indicating darkness of black, for example) is added every pixel of the same position on each see-through image. Then, when the defect detection processing section 32 detects the image whose value of color saturation after addition exceeds a threshold value, the defect detection processing section 32 specifies a position of the solder bump 5 corresponding to that pixel as a place which the tracer (water) permeates by a capillary action, and judges that a crack 8 has occurred in this place.

Further, as shown in FIG. 6, when the defect detection processing section 32 carries out the time lapse processing as the defect detection processing, in the course of the inside of the chamber 14 becoming dry, the defect detection processing section 32 acquires the plurality of see-through images sequentially generated by the see-though image generation section 31 in chronological order, for example, and based on each see-through image having been acquired, specifies positions of the solder bumps 5, for example, on those see-through images. Further, the defect detection processing section 32 observes a decrease amount of a value of a color saturation (darkness of color) corresponding to time lapse every pixel of the same position in the specified region on each see-through image. Then, when the defect detection processing section 32 detects a pixel in which the above-described decrease amount (ratio of decrease) is equal to or less than a threshold value, the defect detection processing section 32 specifies the position of the solder bump 5 corresponding to that pixel as a place which the tracer permeates, and judges that a crack 8 has occurred in this place.

Further, as shown in FIG. 7, when the defect detection processing section 32 carries out the difference observation processing as the defect detection processing, in the course of the inside of the chamber 14 becoming dry, the defect detection processing section 32 acquires the plurality of see-through images sequentially generated by the see-though image generation section 31 in chronological order at a few minutes interval, for example, and sequentially generates difference images of differences between the see-through image at a time that the inside of the chamber 14 becomes completely dry and the see-through images of every several minutes in the course of the inside of the chamber 14 becoming dry. Further, the defect detection processing section 32 observes a decrease amount of a value of a color saturation (darkness of color) corresponding to time lapse of several-minute interval, every pixel of the same position on each see-through image having been sequentially generated. Then, when the defect detection processing section 32 detects a pixel in which the above-described decrease amount is less than a threshold value, the defect detection processing section 32 specifies the position of the solder bump 5 corresponding to that pixel as a place which the tracer (water) permeates, and judges that a crack 8 has occurred in this place.

Here, though examples are explained in which the defect detection processing section 32 detects mainly whether a defect such as a crack 8 exists or not on the solder bump (inspection object) 5 by the defect detection processing such as an integration observation processing, a time lapse processing, and a difference observation processing, a function of the defect detection processing section 32 is not limited thereto. The defect detection processing section 32 may have a function of detecting information of largeness (extension of a crack) of a defect by specifying a size or the like of a region which the tracer permeates, in addition to the function of detecting existence/absence of the defect.

Further, the difference observation processing may include a following processing by man. After 60 minutes have passed, for example, since the start of introduction of the tracer in the vaporized state into the chamber 14, introduction of the tracer is halted by switching of the switching valve 11 and introduction of dry nitrogen gas into the chamber 14 is started. Next, after about 10 minutes have passed, for example, since the start of introduction of the nitrogen gas (after a waterdrop disappears from a surface of the interposer 22 or a surface of the die 21, for example), in the course of the inside of the chamber 14 further drying, the aforementioned difference images are made to displayed every 5 minutes at 0 minute, 5 minutes, 10 minutes, . . . to 60 minutes, and observed by man.

In the difference image at a time of 0 minute, for example, it is supposed that most of a periphery of the solder bump 5 is black since waterdrops probably attach in a space between the die 21 and the interposer 22, for example. Thereafter, time passes, and in the difference image at a time that 35 minutes have passed, for example, influence of the waterdrop becomes little, and on this occasion, if a place which comes out small and black is observed inside a region where the solder bump 5 exists, for example, and further, the place which comes out black is observed also in the difference image at a time that 40 minutes have passed or 45 minutes have passed, for example, and further, water vapor completely vaporizes and the place which comes out black disappears in the difference image at a time that 50 minutes have passed or 55 minutes have passed, for example, it can be supposed that a crack 8 exists in the place which comes out black, the place having been able to be identified until it disappears.

On this occasion, for example, by creating a difference image between the see-through image at the time of 0 minute and the see-through image at the time that 40 minutes have passed and enlarging and analyzing the difference image, it becomes possible to confirm that the above-described place (crack) which comes out small and black exists at a position in detail on an interface between the solder bump 5 and the die 21, for example, and so on. Even by such a difference observation processing including the processing by man, as shown in FIG. 7, since the place which comes out small and black exists at a position corresponding to the solder bump 5 and the place which comes out black disappears as time passes, it is possible to visualize and detect a crack 8 on the solder bump 5 which water permeates by a capillary action.

Figure 8:
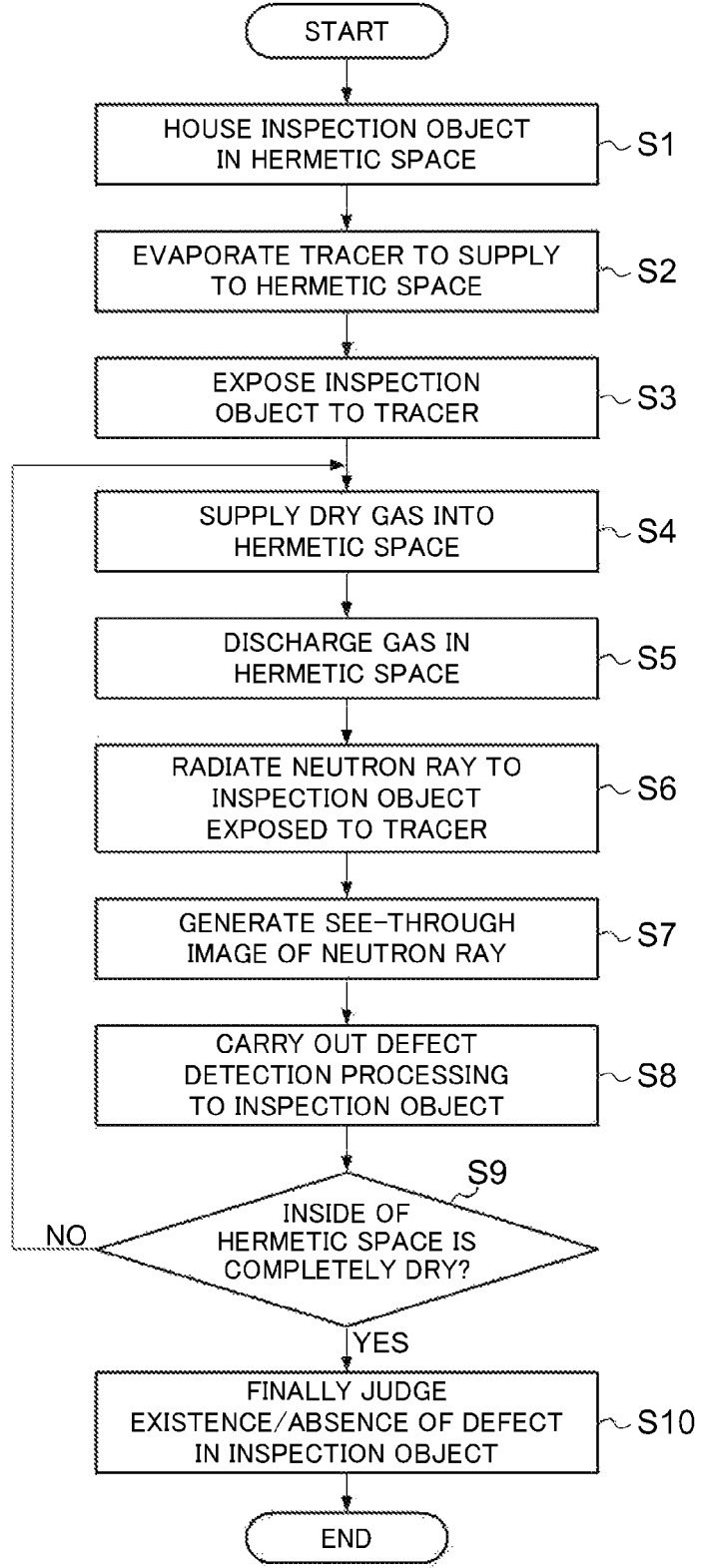
FIG. 8 is a flowchart showing a defect inspection method using the defect inspection device of FIG. 1.

Next, a defect inspection method to which such a defect inspection device 10 is applied will be described based on a flowchart shown in FIG. 8, and FIG. 1, FIG. 6, and so on. First, as shown in FIG. 1 and FIG. 8, after an electronic component 20 is set on a fixing holder 12, a die (bare chip) 21 is encircled between a chamber 14 and an interposer 22 of the electronic component 20, whereby the die 21 including a plurality of solder bumps 5 is housed in a hermetic space 14*a* (S1).

Next, the control section 30 controls a switching valve 11, a pump 18, and a heater 19, to supply a tracer (for example, pure water) such as heavy water and light water in a state of being vaporized from inside a tracer tank 15 into the chamber 14 (hermetic space 14*a*) via a pipe 15*a* (S2). That is, the control section 30 evaporates the tracer to supply to the hermetic space 14a. Note that a temperature of the fixing holder 12 is adjusted to be 60° C., for example, and a temperature of the pipe 15a is adjusted to be 130° C., for example, by the heater 19. Thereby, the tracer is heated to become in a boiling state or over and is vaporized in the course of passing through the pipe 15a. The vaporized tracer (water vapor) flows into the chamber 14 and makes the inside of the chamber 14 be in a humidified state. Thereby, the die 21 including the plurality of solder bumps 5 is exposed to the tracer in the chamber 14 (hermetic space 14a) (S3).

After 30 minutes have passed, for example, since the start of introduction of the tracer into the chamber 14 (for example, after a waterdrop appears on a surface of the interposer 22 or on a surface of the die 21), after further 30 minutes have passed in addition to the above, the control section 30 switches the switching valve 11 to halt the introduction of the tracer and to start supplying of dry nitrogen gas into the chamber 14 from inside a dry gas tank 16 via a pipe 16a (S4). In connection therewith, gas in the chamber 14 (hermetic space 14a) is discharged to an exhaust tank 17 via a pipe 17a (S5). On this occasion, drying of the inside of the chamber 14 is started.

Next, after about 10 minutes have passed, for example, since the start of supplying of dry nitrogen gas into the chamber 14 (for example, after the waterdrop on the surface of the interposer 22 or on the surface of the die 21 disappears), as shown in FIG. 1, a neutron ray is radiated along an arrow Z1 direction to the electronic component 20 including the solder bump (inspection object/target object) 5 exposed to the tracer (S6), and a see-through image generation section 31 sequentially generates a plurality of see-through images (a plurality of neutron images) based on the neutron ray having penetrated the electronic component 20 and the chamber 14 (S7). Subsequently, a defect detection processing section 32 carries out (starts) a defect detection processing for detecting a defect such as a crack 8 which may exist on the solder bump (inspection object) 5 of the electronic component 20 based on the plurality of see-through images sequentially generated, as shown in FIG. 6 or the like (S8).

Further, after the inside of the chamber 14 (hermetic space 14a) becomes completely dry (YES of S9), the defect detection processing section 32 judges YES/NO of existence of the crack 8 in the plurality of solder bumps (inspection objects) 5 from a detection result by a final defect detection processing based on a generated see-through image and the plurality of see-through images having been generated therebefore (S10).

As already described, according to the defect inspection device 10 and the defect inspection method of the present embodiment, since the see-through image is generated from the neutron ray having penetrated the solder bump (inspection object) exposed to the tracer (tracer such as water with a high absorptance for a neutron ray) and the crack on the solder bump is detected based on the generated see-through image, contrast between a solder bump main body and the crack is emphasized, so that a detection accuracy of the crack can be heightened. Further, according to the defect inspection method of the present embodiment, it is possible to accurately detect a defect occurring also in a resin molded article and a metal component, for example, other than the electronic component 20.

Note that, after the defect detection processing, it is possible to verify existence of the crack 8 detected in the defect detection processing, by coating the electronic component 20 with an epoxy resin, cross-section processing a place near the solder bump 5 by mechanical polishing, and further applying a conductive processing to the cross-section processed portion, and thereafter observing by a scanning electron microscope (SEM) or the like.

Figure 9:
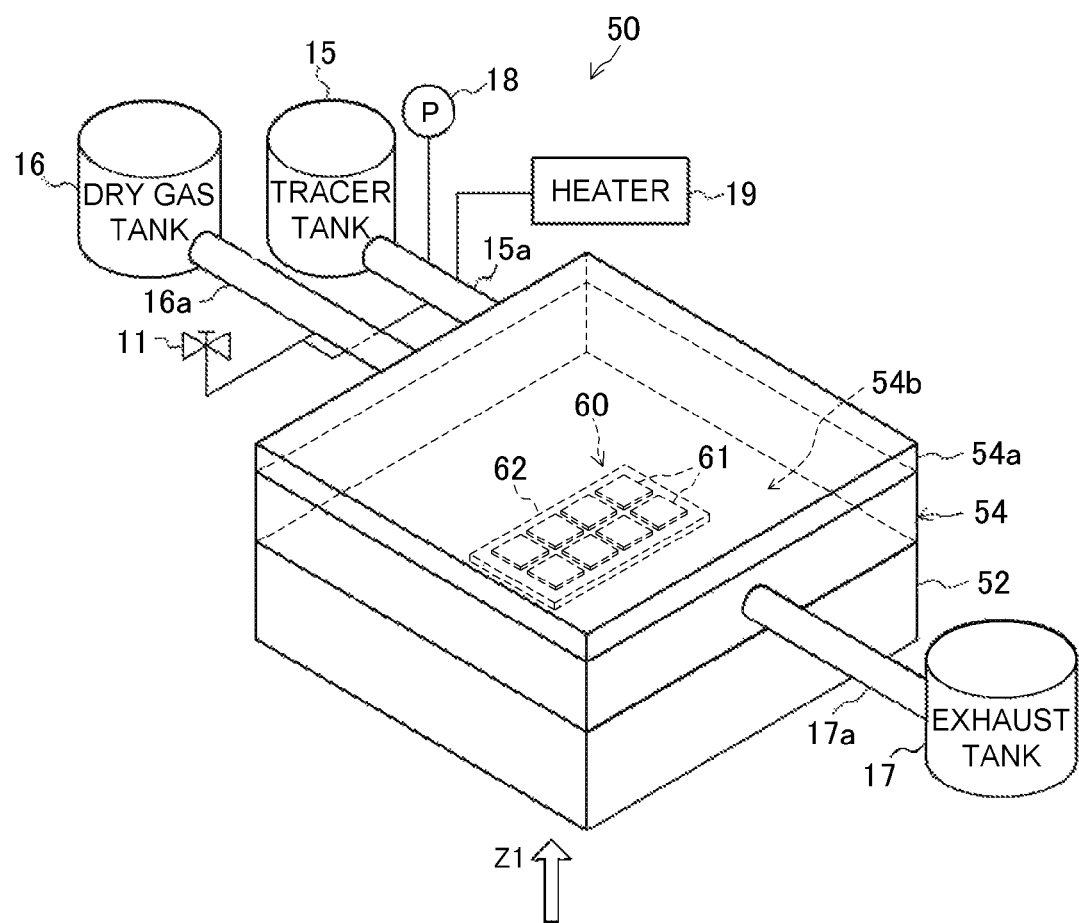
FIG. 9 is a diagram schematically showing a configuration of another defect inspection device different from the defect inspection device of FIG. 1.

Further, it is also possible to apply a defect inspection device 50, as shown in FIG. 9, instead of the aforementioned defect inspection device 10. The defect inspection device 50 is useful for detecting a defect (crack) of a soldered portion in a periphery of each memory chip, with an electronic component (memory device for PC) 60 where a plurality of memory chips 61 are surface-mounted on a wiring substrate 62 being an object.

As shown in FIG. 9, the defect inspection device 50 has a fixing holder 52 and a chamber 54 with a cover 54a, instead of the fixing holder 12 and the chamber 14 of the defect inspection device 10. The chamber 54 houses an entire electronic component 60 in a hermetic space 54a constituted between the chamber 54 and the fixing holder 52. In such a defect inspection device 50 also, similarly to in the defect inspection device 10, it is possible to accurately detect a defect (crack) of a soldered portion (inspection object).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A defect inspection method comprising:
   exposing a target object to a tracer having higher absorptance for a neutron ray than the target object;
   radiating the neutron ray to the target object exposed to the tracer;
   generating at least one neutron image based on the neutron ray having penetrated the target object exposed to the tracer; and
   detecting a defect of the target object based on the generated at least one neutron image.

2. The defect inspection method of claim 1,
   wherein the detecting the defect comprises judging that the defect occurs at a position when detecting the position where the tracer permeates in the target object based on the generated at least one neutron image.

3. The defect inspection method of claim 1,
   wherein, in the exposing, water is used as the tracer.

4. The defect inspection method of claim 1,
   wherein, in the detecting, a crack in a soldered portion is detected as the defect.

5. The defect inspection method of claim 1, further comprising
   drying the tracer after exposing the target object thereto,
   wherein the at least one neutron image comprises a plurality of neutron images;
   wherein, in the radiating, the neutron ray is radiated to the target object during a period of drying the tracer;
   wherein, in the generating, the plurality of neutron images are generated until the tracer is dried; and
   wherein, in the detecting, the defect of the target object is detected based on the generated plurality of neutron images.

6. The defect inspection method of claim 5,
   wherein the exposing comprising:

housing the target object in a hermetic space; and
evaporating the tracer to supply to the hermetic space, and wherein the drying comprising:
supplying dry gas into the hermetic space; and
discharging the gas in the hermetic space.

7. The defect inspection method of claim 1,
wherein the exposing comprising:
housing the target object in a hermetic space; and
evaporating the tracer to supply to the hermetic space.

* * * * *